United States Patent
Koptyaev et al.

(10) Patent No.: US 10,224,688 B2
(45) Date of Patent: Mar. 5, 2019

(54) OPTICAL DUAL-COMB SOURCE APPARATUSES INCLUDING OPTICAL MICRORESONATOR

(71) Applicants: SAMSUNG ELECTRONICS CO., LTD., Suwon-si (KR); INTERNATIONAL CENTER FOR QUANTUM OPTICS & QUANTUM TECHNOLOGIES LIMITED LIABILITY COMPANY, Moscow Reg. (RU)

(72) Inventors: Sergey Nikolaevich Koptyaev, Moscow (RU); Grigoriy Vasil'evich Lihachev, Moscow Reg. (RU); Nikolay Genad'evich Pavlov, Moscow Reg. (RU); Alexey Andreevich Shchekin, Moscow (RU); Igor Antonovich Bilenko, Moscow Reg. (RU); Maxim Vladimirovich Riabko, Moscow (RU); Mikhael Leonidovich Gorodetsky, Moscow Reg. (RU); Stanislav Vladimirovich Polonsky, Moscow (RU); Andrey Sergeevich Voloshin, Moscow Reg. (RU); Alexey Dmitrievich Lantsov, Moscow (RU); Anton Sergeevich Medvedev, Moscow (RU); Valery Evgenievich Lobanov, Moscow (RU)

(73) Assignees: SAMSUNG ELECTRONICS CO., LTD., Suwon-si (KR); INTERNATIONAL CENTER FOR QUANTUM OPTICS & QUANTUM TECHNOLOGIES LIMITED LIABILITY COMPANY, Moscow Reg. (RU)

(*) Notice: Subject to any disclaimer, the term of this patent is extended or adjusted under 35 U.S.C. 154(b) by 0 days.

(21) Appl. No.: 15/870,322

(22) Filed: Jan. 12, 2018

(65) Prior Publication Data
US 2018/0351319 A1    Dec. 6, 2018

(30) Foreign Application Priority Data

May 31, 2017 (RU) .............................. 2017118907
Jul. 18, 2017 (KR) ....................... 10-2017-0091054

(51) Int. Cl.
*G01J 3/28* (2006.01)
*H01S 3/108* (2006.01)
(Continued)

(52) U.S. Cl.
CPC .............. *H01S 3/108* (2013.01); *G01J 3/453* (2013.01); *G01J 4/04* (2013.01); *G01N 21/21* (2013.01);
(Continued)

(58) Field of Classification Search
CPC .... G01J 3/02; G01J 3/28; G01J 3/2803; G01J 3/10; G01J 3/2823
(Continued)

(56) References Cited

U.S. PATENT DOCUMENTS

| 5,748,309 A | 5/1998 | van der Weide et al. |
| 7,203,402 B2 | 4/2007 | Haensch et al. |

(Continued)

FOREIGN PATENT DOCUMENTS

| CN | 103344623 A | 10/2013 |
| EP | 1 988 425 A1 | 11/2008 |

(Continued)

OTHER PUBLICATIONS

Ian Coddington et al., "Dual-comb spectroscopy", Optica, Apr. 14, 2016, pp. 414-426, vol. 3, No. 4, URL: http://dx.doi.org/10.1364/OPTICA.3.000414.
(Continued)

*Primary Examiner* — Md M Rahman
(74) *Attorney, Agent, or Firm* — Sughrue Mion, PLLC

(57) ABSTRACT

Provided is an optical source apparatus that may generate two different optical frequency combs. The optical source apparatus includes an optical resonator and a continuous wave laser emitting laser light having a spectrum component corresponding to a resonance frequency of the optical resonator, and the optical resonator is configured to generate a first frequency comb and a second frequency comb having different modes by interacting with the laser light emitted by the continuous wave laser.

25 Claims, 9 Drawing Sheets

(51) Int. Cl.
    *G01J 3/453*     (2006.01)
    *G01J 4/04*     (2006.01)
    *G01N 21/21*     (2006.01)
    *H01S 3/083*     (2006.01)
    *H01S 3/105*     (2006.01)
    *G02F 1/35*     (2006.01)

(52) U.S. Cl.
    CPC ................ *G02F 1/35* (2013.01); *H01S 3/083* (2013.01); *H01S 3/105* (2013.01)

(58) Field of Classification Search
    USPC .......................................................... 356/326
    See application file for complete search history.

(56) References Cited

U.S. PATENT DOCUMENTS

| | | | |
|---|---|---|---|
| 7,483,143 | B2 | 1/2009 | Sanders et al. |
| 7,982,944 | B2 * | 7/2011 | Kippenberg .............. G02F 1/39 359/245 |
| 8,111,722 | B1 | 2/2012 | Maleki et al. |
| 8,558,993 | B2 | 10/2013 | Newbury et al. |
| 8,564,785 | B2 | 10/2013 | Newbury et al. |
| 8,693,004 | B2 | 4/2014 | Chandler et al. |
| 8,792,525 | B2 | 7/2014 | Fermann et al. |
| 8,831,056 | B2 * | 9/2014 | Savchenkov ............. G04F 5/14 372/18 |
| 9,348,194 | B2 | 5/2016 | Herr et al. |
| 9,490,605 | B2 | 11/2016 | Gaeta et al. |
| 9,509,123 | B2 | 11/2016 | Belkin et al. |
| 9,891,165 | B2 | 2/2018 | Pate et al. |
| 2008/0285606 | A1 * | 11/2008 | Kippenberg .............. G02F 1/39 372/32 |
| 2011/0043815 | A1 | 2/2011 | Giaccari et al. |
| 2011/0261363 | A1 | 10/2011 | Picqué et al. |
| 2013/0003766 | A1 * | 1/2013 | Savchenkov ............. G04F 5/14 372/38.01 |
| 2014/0085632 | A1 * | 3/2014 | Preston ................ G01J 3/0205 356/326 |
| 2014/0192363 | A1 | 7/2014 | Kippenberg et al. |
| 2015/0323450 | A1 | 11/2015 | Lipson et al. |
| 2016/0097963 | A1 | 4/2016 | Fermann et al. |
| 2017/0012705 | A1 | 1/2017 | Vahala et al. |

FOREIGN PATENT DOCUMENTS

| | | |
|---|---|---|
| WO | 2007/092408 A2 | 8/2007 |
| WO | 2011/160013 A1 | 12/2011 |
| WO | 2012/003046 A2 | 1/2012 |
| WO | 2014/131425 A1 | 9/2014 |
| WO | 2017/042439 A1 | 3/2017 |

OTHER PUBLICATIONS

C. Weimann et al., "Fast high-precision distance measurements on scattering technical surfaces using frequency combs", CLEO: Technical Digest, 2013, total 2 pages, CTu2I.3.pdf.

I. Coddington et al., "Rapid and precise absolute distance measurements at long range", Nature Photonics, May 24, 2009, pp. 351-356, vol. 3, DOI: 10.1038/NPHOTON.2009.94.

Birgitta Bernhardt, "Dual Comb Spectroscopy", Dissertation, an der Fakultät für Physik, der Ludwig-Maximilians-Universität, Jun. 20, 2011, total 150 pages, München.

Takuro Ideguchi et al., "Coherent Raman spectro-imaging with laser frequency combs", Nature—Letter, Oct. 17, 2013, pp. 355-359, vol. 502, doi:10.1038/nature12607.

Takuro Ideguchi, "Nonlinear Dual-Comb Spectroscopy", Dissertation, an der Fakultät für Physik, der Ludwig-Maximilians-Universität, Jan. 22, 2014, total 158 pages, München.

Nathan R. Newbury et al., "Sensitivity of coherent dual-comb spectroscopy", Optics Express, Mar. 31, 2010, pp. 7929-7945, vol. 18, No. 8.

Andreas Hugi et al., "All solid state mid-infrared dual-comb spectroscopy platform based on QCL technology", Proceedings of SPIE, SPIE OPTO Conference, 2015, San Francisco, California, United States, vol. 9370, doi: 10.1117/12.2084967, total 7 pages, retrieved from URL: https://www.spiedigitallibrary.org/conference-proceedings-of-spie.

Gustavo Villares et al., "Dual-Comb Spectroscopy based on Quantum Cascade Laser Frequency Combs", Nature Communications, 2014, total 2 pages, vol. 5, No. 5192.

C. Weimann et al., "Silicon Photonic Integrated Circuit for Fast Distance Measurement with Frequency Combs", CLEO, 2014, total 2 pages, STh4O.3.pdf.

W. Liang et al., "Spectrally pure RF photonic source based on a resonant optical hyper-parametric oscillator", Proceedings of SPIE, SPIE LASE Conference, 2014, San Francisco, California, United States, total 9 pages, vol. 8960, doi: 10.1117/12.2044826, retrieved from URL: https://www.spiedigitallibrary.org/conference-proceedings-of-spie.

W. Liang et al., "High spectral purity Kerr frequency comb radio frequency photonic oscillator", Nature Communications, Aug. 11, 2015, pp. 1-8, vol. 6, No. 7957, DOI: 10.1038/ncomms8957.

Theodor W Hansch et al., "Laser Spectroscopy and Frequency Combs", Journal of Physics: Conference Series 467, 2013, pp. 1-7 (total 8 pages), doi:10.1088/1742-6596/467/1/012001.

W. Liang et al., "Whispering-gallery-mode-resonator-based ultranarrow linewidth external-cavity semiconductor laser", Optics Letters, Aug. 15, 2010, pp. 2822-2824, vol. 35, No. 16, Doc. ID 130233.

Avik Dutt et al., "Generation of Dual Frequency Combs using Cascaded Microring Resonators", CLEO, 2016, total 2 pages, SW1E.5.pdf.

Myoung-Gyun Suh et al., "Microresonator Soliton Dual-Comb Spectroscopy", Jul. 27, 2016, arXiv:1607.08222v1 [physics.optics], total 7 pages.

T.J. Kippenberg et al., "Microresonator-Based Optical Frequency Combs", Science, vol. 332, No. 6029, American Association for the Advancement of Science, Apr. 29, 2011, 6 pages.

Communication dated Sep. 21, 2018, issued by the European Patent Office in counterpart European Application No. 18159036.5.

* cited by examiner

OPTICAL DUAL-COMB SOURCE APPARATUSES INCLUDING OPTICAL MICRORESONATOR

CROSS-REFERENCE TO RELATED APPLICATIONS

This application claims priority from Russian Patent Application No. 2017118907, filed on May 31, 2017, in the Russian Patent Office and Korean Patent Application No. 10-2017-0091054, filed on Jul. 18, 2017, in the Korean Intellectual Property Office, the disclosures of which are incorporated herein in their entirety by reference.

BACKGROUND

1. Field

Apparatuses consistent with exemplary embodiments relate relates to optical source apparatuses that generate optical combs, and more particularly, to optical source apparatuses that may generate two different optical frequency combs with a simple structure.

2. Description of the Related Art

A comb-shaped spectrum, in which a large number of optical modes are distributed at certain frequency intervals, is referred to as an optical frequency comb. An optical dual-comb source apparatus generates two optical frequency combs having discrete optical modes at different frequency intervals. Since a dual optical frequency comb may very accurately measure a target object by heterodyne detection, it may be used in any of various fields such as precise optical frequency metrology, spectroscopy, and distance measurement (Light Detection and Ranging (LIDAR)).

In general, a dual optical frequency comb may be generated by using a mode-locked femtosecond laser. However, when a mode-locked femtosecond laser is used, since the volume of an optical dual-comb source apparatus may increase considerably, it may be difficult to apply the optical dual-comb source apparatus to mobile apparatuses or wearable apparatuses.

SUMMARY

One or more exemplary embodiments may provide optical source apparatuses that may generate two different optical frequency combs with a simple structure.

One or more exemplary embodiments may provide optical measurement apparatuses including the optical source apparatuses.

Additional exemplary aspects will be set forth in part in the description which follows and, in part, will be apparent from the description, or may be learned by practice of the presented exemplary embodiments.

According to an aspect of an exemplary embodiment, an optical dual-comb source apparatus includes: laser light source configured to provide first and second laser light; and an optical microresonator including a nonlinear material with a refractive index which varies depending on a light intensity and having a plurality of different resonance modes, wherein the optical microresonator is configured to generate a first optical frequency comb and a second optical frequency comb having different mode intervals by interacting with the first laser light and the second laser light. The first laser light has a spectrum component corresponding to a resonance frequency of a resonance mode related to the first optical frequency comb from among the plurality of different resonance modes of the optical microresonator and the second laser light has a spectrum component corresponding to a resonance frequency of a resonance mode related to the second optical frequency comb.

The optical microresonator may be disk-shaped and have a plurality of different resonance modes depending on depths from a surface of the disk.

The laser light source may include a continuous wave laser having a multimode of simultaneously emitting at least two transverse modes or longitudinal modes of laser light.

The optical dual-comb source apparatus may further include an input/output coupler configured to input the laser light emitted by the continuous wave laser into the optical microresonator and output the first and second optical frequency combs generated by the optical microresonator.

The laser light source may include: a continuous wave laser configured to emit a first laser light having a spectrum component corresponding to a resonance frequency of a resonance mode related to the first optical frequency comb from among the plurality of different resonance modes of the optical microresonator; and an electrooptical modulator configured to modulate the first laser light emitted by the continuous wave laser to generate an optical sideband corresponding to a resonance frequency of a resonance mode related to the second optical frequency comb from among the plurality of different resonance modes of the optical microresonator.

The laser light source may include: a first continuous wave laser configured to emit first laser light having a spectrum component corresponding to a resonance frequency of a resonance mode related to the first optical frequency comb from among the plurality of different resonance modes of the optical microresonator; and a second continuous wave laser configured to emit second laser light having a spectrum component corresponding to a resonance frequency of a resonance mode related to the second optical frequency comb from among the plurality of different resonance modes of the optical microresonator.

The optical dual-comb source apparatus may further include: a beam coupler configured to couple the first laser light and the second laser light to propagate a coupling result thereof through an optical path; and an input/output coupler configured to input the first and second laser light to the optical microresonator and output the first and second optical frequency combs generated by the optical microresonator.

The optical dual-comb source apparatus may further include: an input/output coupler configured to input the first laser light into the optical microresonator and output the first and second optical frequency combs generated by the optical microresonator; and an input coupler configured to input the second laser light into the optical microresonator.

The optical dual-comb source apparatus may further include: a first input/output coupler configured to input the first laser light into the optical microresonator and output the first optical frequency comb generated by the optical microresonator; and a second input/output coupler configured to input the second laser light into the optical microresonator and output the second optical frequency comb generated by the optical microresonator.

According to an aspect of another exemplary embodiment, an optical dual-comb source apparatus includes: laser light source configured to provide first laser light and second laser light; and first and second optical microresonators including a nonlinear material with a refractive index which varies depending on light intensity, wherein the first and second optical microresonators are configured to generate a first optical frequency comb and a second optical frequency comb having different mode intervals by interacting with the first laser light and the second laser light, and the first laser light has a spectrum component corresponding to a resonance frequency of a resonance mode related to the first optical frequency comb from among a plurality of different resonance modes of the optical microresonator and the second laser light has a spectrum component corresponding to a resonance frequency of a resonance mode related to the second optical frequency comb.

The laser light source may include a continuous wave laser having a multimode of simultaneously emitting at least two transverse modes or longitudinal modes of laser light.

The optical dual-comb source apparatus may further include an input/output coupler configured to input the laser light emitted by the continuous wave laser into each of the first and second optical microresonators and output the first and second optical frequency combs generated by the first and second optical microresonators.

The laser light source may include: a continuous wave laser configured to emit a first laser light having a spectrum component corresponding to a resonance frequency of a resonance mode related to the first optical frequency comb from among the plurality of different resonance modes of the optical microresonator; and an electrooptical modulator configured to modulate the first laser light emitted by the continuous wave laser to generate an optical sideband corresponding to a resonance frequency of a resonance mode related to the second optical frequency comb from among the plurality of different resonance modes of the optical microresonator.

The first and second optical microresonators may include similar disk-shaped resonators and having a plurality of different resonance modes depending a depths from a surface of the disk.

The first optical microresonator may have a resonance mode related to the first optical frequency comb, the second optical microresonator may have a resonance mode related to the second optical frequency comb, and the first optical microresonator and the second optical microresonator may each be disk-shaped with different respective diameters.

The optical dual-comb source apparatus may further include: an input coupler configured to input the laser light emitted by the continuous wave laser to each of the first and second optical microresonators; a first output coupler configured to output the first optical frequency comb generated by the first optical microresonator; and a second output coupler configured to output the second optical frequency comb generated by the second optical microresonator.

The optical dual-comb source apparatus may further include: a first input/output coupler configured to input the laser light emitted by the continuous wave laser into the first optical microresonator and output the first optical frequency comb generated by the first optical microresonator; and a second input/output coupler configured to input the laser light emitted by the continuous wave laser into the second optical microresonator and output the second optical frequency comb generated by the second optical microresonator.

The optical dual-comb source apparatus may further include: a first input coupler configured to input the laser light emitted by the continuous wave laser into the first optical microresonator; a second input coupler configured to input the laser light emitted by the continuous wave laser into the second optical microresonator; a first output coupler configured to output the first optical frequency comb generated by the first optical microresonator; and a second output coupler configured to output the second optical frequency comb generated by the second optical microresonator.

The laser light source may include: a first continuous wave laser configured to emit first laser light; and a second continuous wave laser configured to emit second laser light.

The optical dual-comb source apparatus may further include: a first input coupler configured to input the first laser light emitted by the first continuous wave laser into the first optical microresonator; a second input coupler configured to input the second laser light emitted by the second continuous wave laser into the second optical microresonator; a first output coupler configured to output the first optical frequency comb generated by the first optical microresonator; and a second output coupler configured to output the second optical frequency comb generated by the second optical microresonator.

The optical dual-comb source apparatus may further include: a first input coupler configured to input the first laser light emitted by the first continuous wave laser into the first optical microresonator; a second input coupler configured to input the second laser light emitted by the second continuous wave laser into the second optical microresonator; and an output coupler configured to output the first and second optical frequency combs generated respectively by the first and second optical microresonators.

The optical dual-comb source apparatus may further include: a first input/output coupler configured to input the first laser light emitted by the first continuous wave laser into the first optical microresonator and output the first optical frequency comb generated by the first optical microresonator; and a second input/output coupler configured to input the second laser light emitted by the second continuous wave laser into the second optical microresonator and output the second optical frequency comb generated by the second optical microresonator.

According to an aspect of another exemplary embodiment, an optical measurement apparatus includes: an optical dual-comb source apparatus having the above configuration; a first beam splitter configured to split the first optical frequency comb into a probe frequency comb and a reference frequency comb; a second beam splitter configured to split the second optical frequency comb into two optical frequency combs; a first beam coupler configured to generate a third optical frequency comb by coupling the probe frequency comb, which has been transmitted through or reflected or scattered by a measurement target, to one of the split second optical frequency combs; a second beam coupler configured to generate a fourth optical frequency comb by coupling the reference frequency comb to another of the split second optical frequency combs; a first photodetector configured to measure the third optical frequency comb; and a second photodetector configured to measure the fourth optical frequency comb.

According to an aspect of another exemplary embodiment, an optical measurement apparatus includes: an optical dual-comb source apparatus having the above configuration; a first beam splitter configured to split the first optical frequency comb into a probe frequency comb and a reference frequency comb; a first beam coupler configured to couple the probe frequency comb, which has been transmitted through or reflected or scattered by a measurement target, to the reference frequency comb; a second beam coupler configured to generate a third optical frequency comb by coupling the probe frequency comb and the reference frequency comb coupled by the first beam coupler to the second optical frequency comb; and a photodetector configured to measure the third optical frequency comb.

According to an aspect of another exemplary embodiment, an optical measurement apparatus includes: an optical dual-comb source apparatus having the above configuration; a beam coupler configured to couple the first optical frequency comb and the second optical frequency comb to generate a frequency comb; a beam splitter configured to split the first optical frequency comb and the second optical frequency comb coupled by the beam coupler into a probe frequency comb and a reference frequency comb; a first photodetector configured to measure the probe frequency comb that has been transmitted through or reflected or scattered by a measurement target; and a second photodetector configured to measure the reference frequency comb.

According to an aspect of another exemplary embodiment, an optical measurement apparatus includes: an optical dual-comb source apparatus having the above configuration; a first beam coupler configured to couple the first optical frequency comb and the second optical frequency comb to generate a frequency comb; a beam splitter configured to split the first optical frequency comb and the second optical frequency comb coupled by the beam coupler into a probe frequency comb and a reference frequency comb; a second beam coupler configured to couple the probe frequency comb, which has been transmitted through or reflected or scattered by a measurement target, to the reference frequency comb; and a photodetector configured to measure the coupled probe frequency comb and reference frequency comb.

BRIEF DESCRIPTION OF THE DRAWINGS

These and/or other exemplary aspects and advantages will become apparent and more readily appreciated from the following description of the exemplary embodiments, taken in conjunction with the accompanying drawings in which.

DETAILED DESCRIPTION

Figure 1:
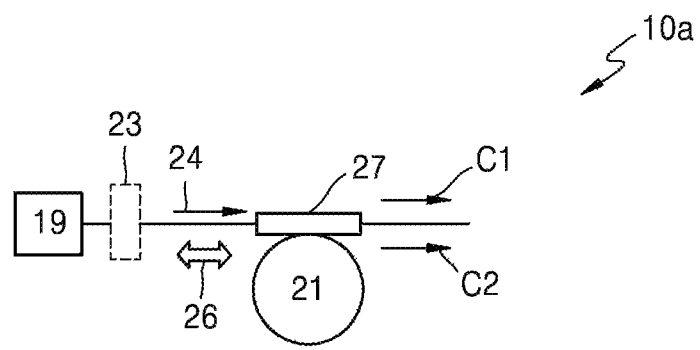
FIG. 1 is a schematic block diagram illustrating a configuration of an optical dual-comb source apparatus including a laser, according to an exemplary embodiment.

Reference will now be made in detail to exemplary embodiments which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, optical dual-comb source apparatuses including optical microresonators according to exemplary embodiments will be described in detail with reference to the accompanying drawings. In the drawings, like reference numerals may denote like elements, and the size of each element may be exaggerated for clarity and convenience of description. Also, the exemplary embodiments described below are merely examples, and various modifications may be made therein. Also, in a layer structure described below, the terms "over" or "on" may include not only "directly over" or "directly on" but also "indirectly over" or "indirectly on".

FIG. 1 is a schematic block diagram illustrating a configuration of an optical dual-comb source apparatus including a laser, according to an exemplary embodiment. Referring to FIG. 1, an optical dual-comb source apparatus 10a according to an exemplary embodiment may include a laser 19 configured to emit laser light 24, an optical microresonator 21 configured to resonate the laser light 24 to generate two optical frequency combs C1 and C2, and an input/output coupler 27 configured to couple the laser light 24 to the optical microresonator 21 and output the optical frequency combs C1 and C2 generated by the optical microresonator 21.

The laser 19 may be a continuous wave laser that may continue to oscillate with a constant output in time. For example, the laser 19 may be a semiconductor laser diode that may be manufactured in a small size, and the light power of the laser 19 may be greater than a pump threshold value capable of pumping the optical microresonator 21. Also, the laser 19 may be a multimode laser that simultaneously emits two or more transverse modes or longitudinal modes of light, or may be a dual-frequency laser that simultaneously emits light having two frequencies. In this case, the laser 19 may emit laser light 24 having spectrum components corresponding to resonance frequencies of two resonance modes related to the optical frequency combs C1 and C2, from among a plurality of different resonance modes of the optical microresonator 21.

Alternatively, the laser 19 may be a continuous wave laser that emits laser light 24 having a spectrum component corresponding to a resonance frequency of only one resonance mode from among a plurality of resonance modes of the optical microresonator 21. In this case, the optical dual-comb source apparatus 10a may further include an electrooptical modulator 23 arranged on an optical path between the laser 19 and the optical microresonator 21. The electrooptical modulator 23 may modulate the laser light 24 incident on the electrooptical modulator 23 to generate an optical sideband corresponding to a resonance frequency of another resonance mode of the optical microresonator 21. Then, the laser light 24 passing through the optical microresonator 23 may have spectrum components corresponding to resonance frequencies of two resonance modes related to the optical frequency combs C1 and C2, from among the plurality of resonance modes of the optical microresonator 21. For example, the laser 19 may emit laser light 24 having a spectrum component corresponding to a resonance frequency of a resonance mode related to the first optical frequency comb C1, and the electrooptical modulator 23 may generate an optical sideband corresponding to a resonance frequency of a resonance mode related to the second optical frequency comb C2. Herein, the laser 19 and the electrooptical resonator 23 may be regarded as, together, constituting the laser light source. On the other hand, when the laser 19 is a multimode laser, just one laser 19 may constitute the laser light source.

The optical microresonator 21 may have the shape of a disk with a diameter of about 0.1 mm to about 10 mm. Also, the optical microresonator 21 may include a nonlinear material with a refractive index that is different depending on a light intensity (i.e., an intensity-dependent refractive index). The optical microresonator 21 may have different effective resonator radii depending on depths from a disk surface. That is, the optical microresonator 21 may have a plurality of different resonance modes depending on depths from a surface thereof, and each resonance mode may have a slightly different resonance frequency. When light having a spectrum component corresponding to a resonance frequency of any one resonance mode, from among the plurality of resonance modes, is coupled to the optical microresonator 21, a parametric oscillation occurs. As a result, a large number of sidebands are generated at certain intervals in a frequency domain to generate an optical frequency comb. The interval in the frequency domain may be referred to as mode interval (mode spacing) or a free spectral range, and it may be defined as an effective resonator radius like $c/2\pi \cdot n$. Herein, "c" denotes the velocity of light, "r" denotes an effective radius of a resonator, and "n" denotes a refractive index of a resonator material.

Also, optical frequency combs having slightly different mode intervals may be generated according to the resonance modes of the optical microresonator 21. Thus, when laser light 24 having two spectrums corresponding, respectively, to resonance frequencies of two different resonance modes, from among the plurality of resonance modes of the optical microresonator 21, is provided to the optical microresonator 21, two optical frequency combs C1 and C2 having slightly different mode intervals may be generated.

The two generated optical frequency combs C1 and C2 may be output outside the optical microresonator 21 through the input/output coupler 27. In the present exemplary embodiment, the input/output coupler 27 may simultaneously perform the functions of an input coupler and an output coupler. The input/output coupler 27 may include, for example, an optical fiber or a prism arranged at an outer periphery of the optical microresonator 21.

If desired, the optical dual-comb source apparatus 10a may further include a locking mechanism 26 configured to lock a frequency of the laser light 24 to a resonance frequency of a selected resonance mode of the optical microresonator 21. For example, the locking mechanism 26 may adopt a self-injection locking scheme that returns a portion of the light, which is output after resonating in the optical microresonator 21, to the laser 19. When the locking mechanism 26 is used, the light power of the laser light 24 emitted by the laser 19 is redistributed around the resonance frequency of the selected resonance mode of the optical microresonator 21. As a result, since the spectrum component of the laser light 24 incident on the optical microresonator 21 may be concentrated on the resonance frequency of the selected resonance mode of the optical microresonator 21, the pumping efficiency of the optical microresonator 21 for generating the optical frequency combs C1 and C2 may be improved.

As described above, according to the present exemplary embodiment, two optical frequency combs C1 and C2 may be generated by just one laser 19 and just one optical microresonator 21. Thus, the optical dual-comb source apparatus 10a may be miniaturized. In addition, since the laser 19 is a small semiconductor laser diode and the optical microresonator 21 has a very small size, the optical dual-comb source apparatus 10a may be made to be very small by integrating the laser 19, the optical microresonator 21, and the input/output coupler 27 into a semiconductor chip. Thus, the optical dual-comb source apparatus 10a may be applied to mobile apparatuses or wearable apparatuses. Also, since only one optical microresonator 21 is used, it may not be necessary to accurately match two resonators with sub-micron accuracy. Also, it may be possible to generate a visible-ray, ultraviolet-ray, or infrared-ray range of optical frequency combs C1 and C2 according to the design of the laser 19 and the optical microresonator 21.

Figure 2:
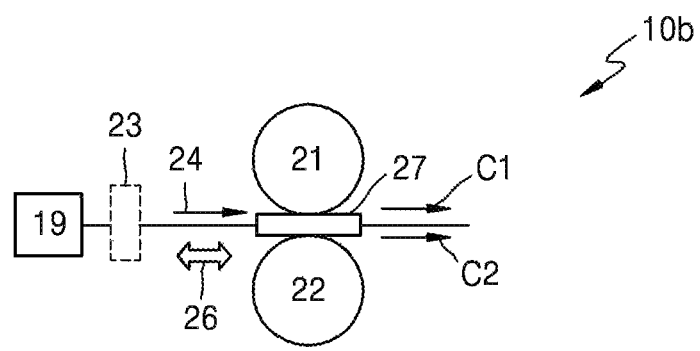
FIGS. 2, 3, and 4 are schematic block diagrams illustrating configurations of optical dual-comb source apparatuses including a laser, according to exemplary embodiments.

FIG. 2 is a schematic block diagram illustrating a configuration of an optical dual-comb source apparatus 10b including a laser 19, according to another exemplary embodiment. Referring to FIG. 2, the optical dual-comb source apparatus 10b may include a laser 19, two optical microresonators 21 and 22, and an input/output coupler 27. In the present exemplary embodiment, the first optical microresonator 21 and the second optical microresonator 22 may be respectively arranged such that each one is adjacent one of the two sides of the input/output coupler 27. Also, as described above, if necessary, the optical dual-comb source apparatus 10b may further include an electrooptical modulator 23 and a locking mechanism 26.

Laser light 24 emitted by the laser 19 may be supplied to each of the first optical microresonator 21 and the second optical microresonator 22 through the input/output coupler 27. Herein, the laser light 24 incident on the input/output coupler 27 may have spectrum components corresponding to resonance frequencies related to two target optical frequency combs C1 and C2. The first optical microresonator 21 and the second optical microresonator 22 may be the same resonators having a plurality of resonance modes. In this case, both of the two optical frequency combs C1 and C2 may be generated by each of the first optical microresonator 21 and the second optical microresonator 22. Alternatively, the first optical microresonator 21 may have a resonance mode related to the first optical frequency comb C1, and the second optical microresonator 22 may have a resonance mode related to the second optical frequency comb C2. For example, a diameter of the first optical microresonator 21 and a diameter of the second optical microresonator 22 may be different from each other. In this case, only the first optical frequency comb C1 may be generated by the first optical microresonator 21, and only the second optical frequency comb C2 may be generated by the second optical microresonator 22. The generated first and second optical frequency combs C1 and C2 may be output through the input/output coupler 27.

Figure 3:
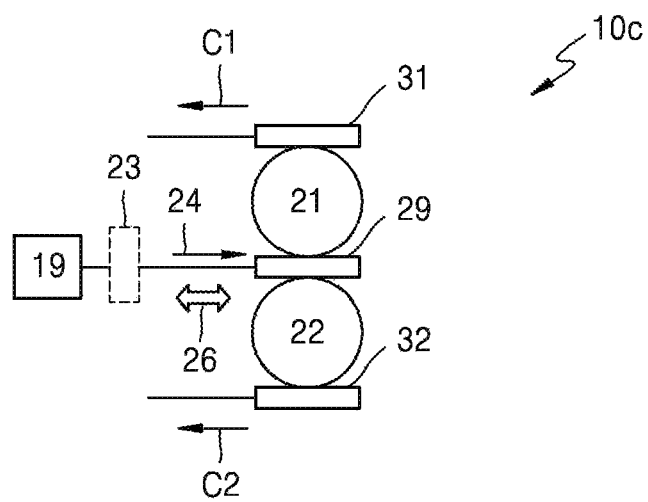

FIG. 3 is a schematic block diagram illustrating a configuration of an optical dual-comb source apparatus 10c including a laser 19, according to another exemplary embodiment. Referring to FIG. 3, the optical dual-comb source apparatus 10c may include a laser 19, two optical microresonators 21 and 22, an input coupler 29, and two output couplers 31 and 32. In the present exemplary embodiment, the two optical microresonators 21 and 22 may share the input coupler 29 and may have each their respective separate output couplers 31 and 32. For example, the first optical microresonator 21 and the second optical microresonator 22 may be respectively arranged adjacent to both sides of the input coupler 29, the first output coupler 31 may be arranged at an outer periphery of the first optical microresonator 21, and the second output coupler 32 may be arranged at an outer periphery of the second optical microresonator 22.

Also, the first optical microresonator 21 may have a resonance mode related to a first optical frequency comb C1, and the second optical microresonator 22 may have a resonance mode related to a second optical frequency comb C2. To do so, a diameter of the first optical microresonator 21 and a diameter of the second optical microresonator 22 may be different from each other. In this case, only the first optical frequency comb C1 may be generated by the first optical microresonator 21, and only the second optical frequency comb C2 may be generated by the second optical microresonator 22. Thereafter, the first optical frequency comb C1 generated by the first optical microresonator 21 may be output through the first output coupler 31, and the second optical frequency comb C2 generated by the second optical microresonator 22 may be output through the second output coupler 32.

Figure 4:
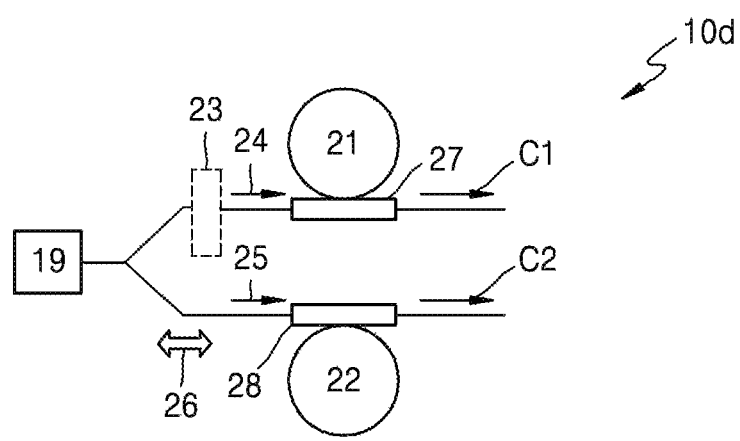

FIG. 4 is a schematic block diagram illustrating a configuration of an optical dual-comb source apparatus 10d including a laser 19, according to another exemplary embodiment. Referring to FIG. 4, the optical dual-comb source apparatus 10d may include a laser 19, two optical microresonators 21 and 22, and two input/output couplers 27 and 28. For example, the first input/output coupler 27 may be arranged adjacent to an outer periphery of the first optical microresonator 21, and the second input/output coupler 28 may be arranged adjacent to an outer periphery of the second optical microresonator 22.

Light emitted by the laser 19 may, for example, be split into laser light 24 and laser light 25 by a beam splitter (not illustrated) or two optical fibers. The split first laser light 24 may be supplied to the first optical microresonator 21 through the first input/output coupler 27, and the split second laser light 25 may be supplied to the second optical microresonator 22 through the second input/output coupler 28. An electrooptical modulator 23 may be further arranged on an optical path of the first laser light 24 before the first input/output coupler 27. The electrooptical modulator 23 may modulate the first laser light 24 to generate an optical sideband corresponding to a resonance frequency of the first optical microresonator 21. However, when the laser 19 is a dual frequency laser or a multimode laser, the electrooptical modulator 23 may be omitted. Also, if necessary, a locking mechanism 26 configured to lock a frequency of the second laser light 25 to a resonance frequency of the second optical microresonator 22 may be arranged on an optical path of the second laser light 25.

The first optical microresonator 21 may have a resonance mode related to a first optical frequency comb C1, and the second optical microresonator 22 may have a resonance mode related to a second optical frequency comb C2. In this case, only the first optical frequency comb C1 may be generated by the first optical microresonator 21, and only the second optical frequency comb C2 may be generated by the second optical microresonator 22. Thereafter, the first optical frequency comb C1 generated by the first optical microresonator 21 may be output through the first input/output coupler 27, and the second optical frequency comb C2 generated by the second optical microresonator 22 may be output through the second input/output coupler 28.

Figure 5:
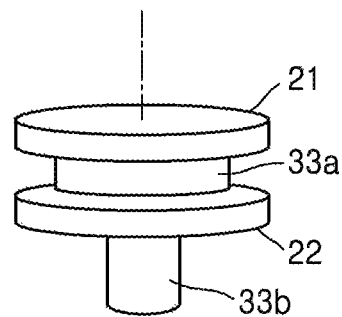
FIG. 5 is a schematic perspective view illustrating a structure of two optical microresonators illustrated in FIG. 4.

Although FIGS. 2 to 4 illustrate that the two optical microresonators 21 and 22 are separate resonators separated from each other, the two optical microresonators 21 and 22 may also be configured as one single body. For example, FIG. 5 is a schematic perspective view illustrating a structure of the two optical microresonators 21 and 22 illustrated in FIG. 4. Referring to FIG. 5, the first optical microresonator 21 and the second optical microresonator 22 each having a shape of a circular disk may be arranged parallel to each other, one above the other on a common center axis. A spacer 33a may be further arranged between the first optical microresonator 21 and the second microresonator 22 so that the first optical microresonator 21 and the second microresonator 22 may be spaced apart from each other. The spacer 33a may be arranged along a center axis of the first optical microresonator 21 and the second optical microresonator 22. Also, a diameter of the spacer 33a may be less than a diameter of the first optical microresonator 21 and the second optical microresonator 22. According to exemplary embodiments, a diameter of the first optical microresonator 21 may be equal to or different from a diameter of the second optical microresonator 22.

Also, for convenience of carrying, installing, assembling, and fixing the first optical microresonator 21 and the second optical microresonator 22, a pivot pin 33b may be further formed to extend and protrude from a center axis of the second optical microresonator 22 in a vertical direction with respect to a surface of the second optical microresonator 22. Also, a diameter of the pivot pin 33b may be less than a diameter of the first optical microresonator 21 and the second optical microresonator 22. Also, the pivot pin 33b may be located on an opposite side of the spacer 33a with respect to the second optical microresonator 22. All of the first optical microresonator 21, the second optical microresonator 22, the spacer 33a, and the pivot pin 33b may be integrally formed of the same material and may be arranged on a common center axis.

Figure 6:
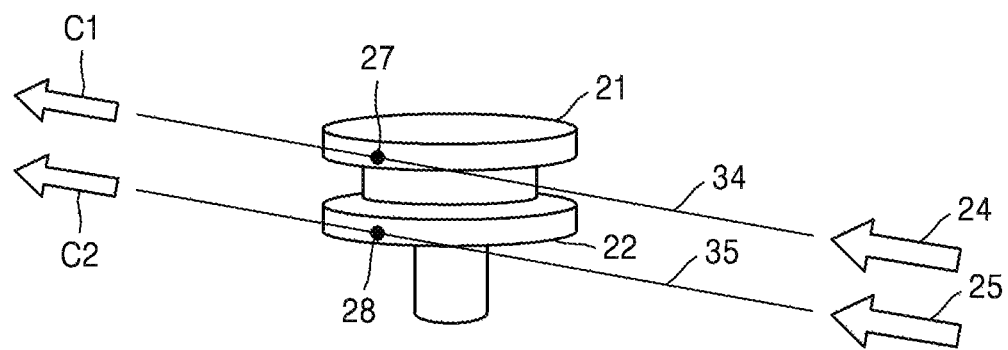
FIG. 6 is a perspective view illustrating an example of coupling two laser light to two optical microresonators illustrated in FIG. 5.

FIG. 6 is a perspective view illustrating an example of coupling the laser light 24 and the laser light 25 to the two optical microresonators 21 and 22 illustrated in FIG. 5. Referring to FIG. 6, the first laser light 24 may propagate through a first optical fiber 34. The first optical fiber 34 may contact a region of an outer periphery of the first optical microresonator 21, and a portion of the first optical fiber 34 contacting the outer periphery of the first optical microresonator 21 may function as the first input/output coupler 27. The first laser light 24 may be supplied to the first optical microresonator 21 through the first input/output coupler 27. Also, the first optical frequency comb C1 generated by the first optical microresonator 21 may propagate along the first optical fiber 34 after being output from the first input/output coupler 27 to the first optical fiber 34. Likewise, the second laser light 25 may propagate along a second optical fiber 35. The second optical fiber 35 may contact a region of an outer periphery of the second optical microresonator 22, and a portion of the second optical fiber 35 contacting the outer periphery of the second optical microresonator 22 may function as the second input/output coupler 28. The second laser light 25 may be supplied to the second optical microresonator 22 through the second input/output coupler 28, and the second optical frequency comb C2 generated by the second optical microresonator 22 may propagate along the second optical fiber 35 after being output from the second input/output coupler 28 to the second optical fiber 35.

Figure 7:
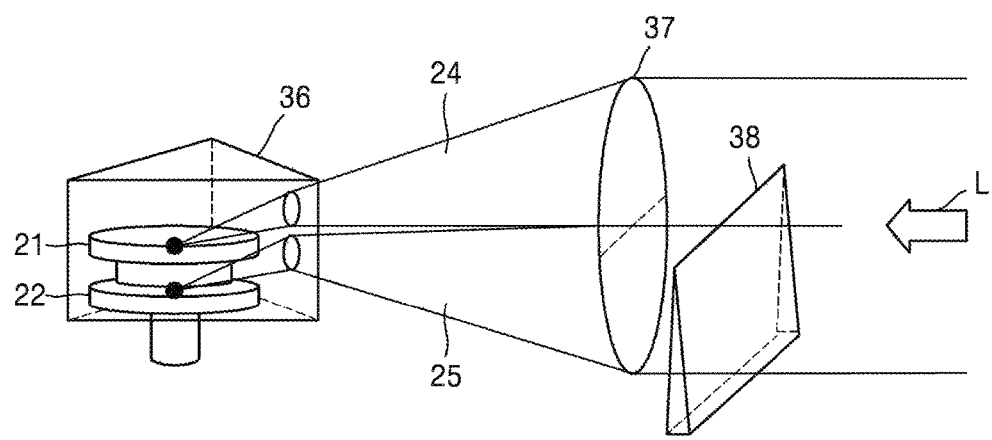
FIG. 7 is a perspective view illustrating another example of coupling two laser light to two optical microresonators illustrated in FIG. 5.

Also, FIG. 7 is a perspective view illustrating another example of coupling the laser light 24 and the laser light 25 to the two optical microresonators 21 and 22 illustrated in FIG. 5. Referring to FIG. 7, laser light L emitted by the laser 19 may be split by a wedge-type beam splitter 38 into the first laser light 24 and the second laser light 25. For example, the wedge-type beam splitter 38 may be arranged only in half of a region of a beam cross section of the laser light L. Then, a portion of the laser light L not passing through the wedge-type beam splitter 38 may become the first laser light 24, and a portion of the laser light L passing through the wedge-type beam splitter 38 may become the second laser light 25 after a propagation direction thereof is changed. Each of the first laser light 24 and the second laser light 25 may be focused by a lens 37 and then incident on an input/output coupler 36 having a prism shape. Thereafter, the first laser light 24 and the second laser light 25 may be refracted by the input/output coupler 36 to be incident on a point of an outer periphery of the first optical microresonator 21 and a point of an outer periphery of the second optical microresonator 22 and then supplied to the first optical microresonator 21 and the second optical microresonator 22, respectively.

Figure 8:
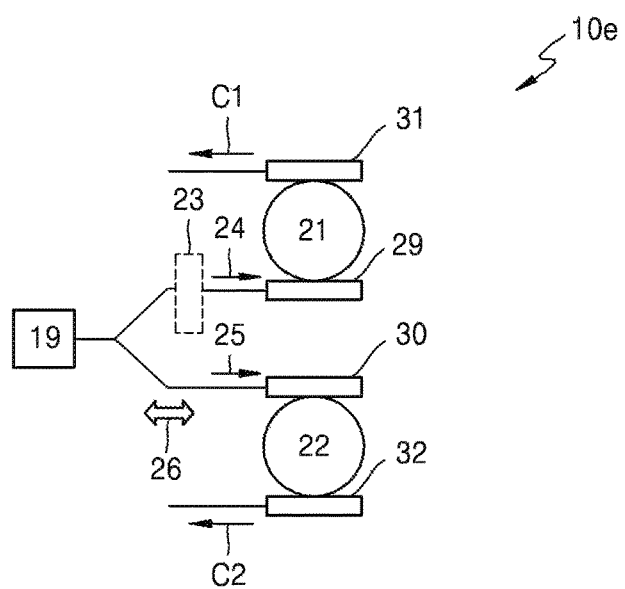
FIG. 8 is a schematic block diagram illustrating a configuration of an optical dual-comb source apparatus including a laser, according to another exemplary embodiment.

FIG. 8 is a schematic block diagram illustrating a configuration of an optical dual-comb source apparatus 10e including a laser 19, according to another exemplary embodiment. Referring to FIG. 8, the optical dual-comb source apparatus 10e may include a laser 19, two optical microresonators 21 and 22, two input couplers 29 and 30, and two output couplers 31 and 32. For example, the first input coupler 29 and the first output coupler 31 may be respectively arranged adjacent to different points on an outer periphery of the first optical microresonator 21. Likewise, the second input coupler 30 and the second output coupler 32 may be arranged adjacent to different points on an outer periphery of the second optical microresonator 22. An electrooptical modulator 23 may be further arranged on an optical path of the first laser light 24 before the first input/output coupler 27. The electrooptical modulator 23 may modulate the first laser light 24 to generate an optical sideband corresponding to a resonance frequency of the first optical microresonator 21.

Laser light emitted by the laser 19 may, for example, be split into laser light 24 and laser light 25 by the two optical fibers 34 and 35 illustrated in FIG. 6 or by the wedge-type beam splitter 38 illustrated in FIG. 7. The split first laser light 24 may be supplied to the first optical microresonator 21 through the first input coupler 29, and the first optical frequency comb C1 generated by the first optical microresonator 21 may be output through the first output coupler 31. Also, likewise, the split second laser light 25 may be supplied to the second optical microresonator 22 through the second input coupler 30, and the second optical frequency comb C2 generated by the second optical microresonator 22 may be output through the second output coupler 32.

Figure 9:
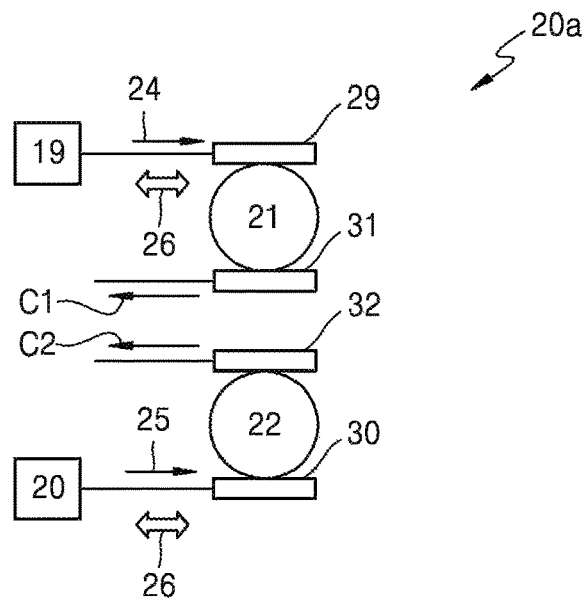
FIGS. 9, 10, 11, 12, 13, and 14 are schematic block diagrams illustrating configurations of optical dual-comb source apparatuses including two lasers, according to other exemplary embodiments.
Figure 10:
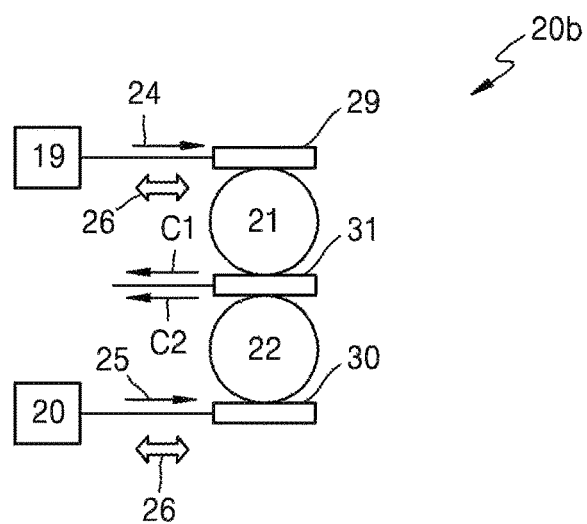
Figure 11:
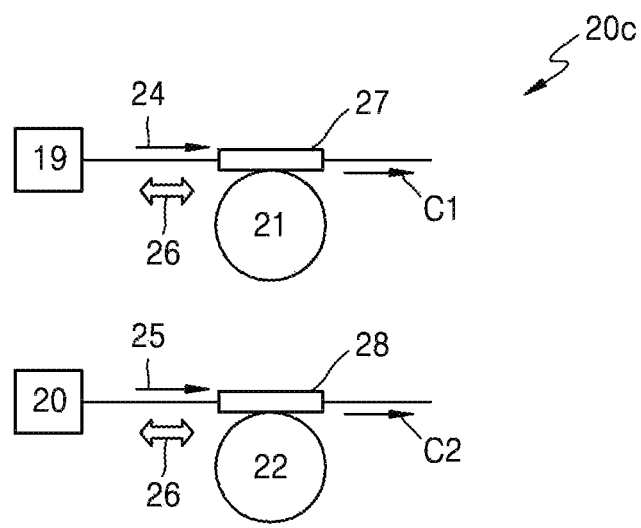
Figure 12:
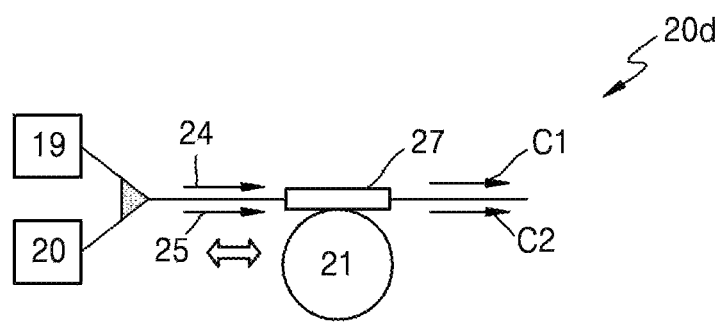
Figure 13:
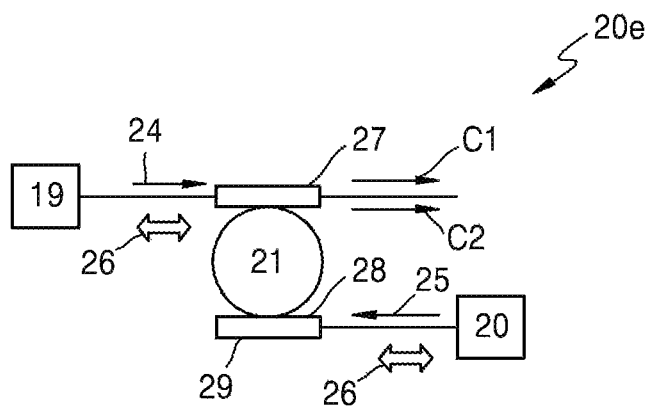
Figure 14:
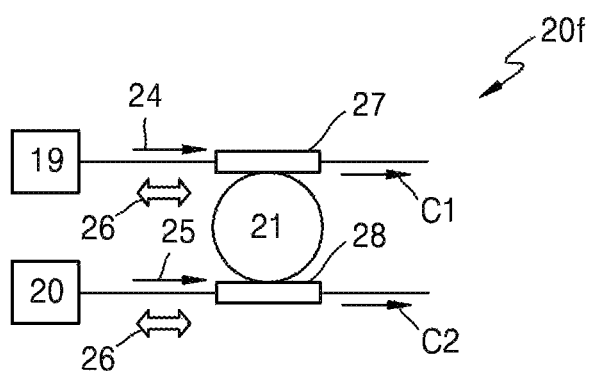

FIGS. 9 to 14 are schematic block diagrams illustrating configurations of optical dual-comb source apparatuses including two lasers, according to other exemplary embodiments. In particular, FIGS. 9 to 11 illustrate examples of an optical dual-comb source apparatus using two lasers and two optical microresonators, and FIGS. 12 to 14 illustrate examples of an optical dual-comb source apparatus using two lasers and an optical microresonator.

First, referring to FIG. 9, an optical dual-comb source apparatus 20a may include two lasers 19 and 20, two optical microresonators 21 and 22, two input couplers 29 and 30, and two output couplers 31 and 32. In the present exemplary embodiment, the first optical microresonator 21 may have a resonance mode related to a first optical frequency comb C1, and the second optical microresonator 22 may have a resonance mode related to a second optical frequency comb C2. For example, a diameter of the first optical microresonator 21 and a diameter of the second optical microresonator 22 may be different from each other. Also, the first laser 19 may emit a first laser light 24 having a spectrum component corresponding to a resonance frequency of the first optical microresonator 21, and the second laser 20 may emit a second laser light 25 having a spectrum component corresponding to a resonance frequency of the second optical microresonator 22. Thus, the first laser 19 and the second laser 20 may together constitute laser light source.

Also, the optical dual-comb source apparatus 20a may further include a locking mechanism 26 configured to lock a frequency of the first laser light 24 to a resonance frequency of the first optical microresonator 21 and lock a frequency of the second laser light 25 to a resonance frequency of the second optical microresonator 22. However, the optical dual-comb source apparatus 20a according to the present exemplary embodiment may omit the electrooptical modulator 23.

In the optical dual-comb source apparatus 20a illustrated in FIG. 9, the first laser light 24 emitted from the first laser 19 may be supplied to the first optical microresonator 21 through the first input coupler 29, and the first optical frequency comb C1 generated by the first optical microresonator 21 may be output through the first output coupler 31. Also, likewise, the second laser light 25 emitted from the second laser 20 may be supplied to the second optical microresonator 22 through the second input coupler 30, and the second optical frequency comb C2 generated by the second optical microresonator 22 may be output through the second output coupler 32.

Referring to FIG. 10, an optical dual-comb source apparatus 20b may include two lasers 19 and 20, two optical microresonators 21 and 22, two input couplers 29 and 30, and an output coupler 31. In the present exemplary embodiment, the two optical microresonators 21 and 22 may share the output coupler 31 and may have their respective separate input couplers 29 and 30. For example, the first optical microresonator 21 and the second optical microresonator 22 may be arranged such that an outer periphery of the first optical microresonator 21 and an outer periphery of the second optical microresonator 22 each contact one of two sides of the output coupler 31. Also, the first input coupler 29 may be arranged at another outer periphery of the first optical microresonator 21, and the second input coupler 30 may be arranged at an outer periphery of the second optical microresonator 22. Then, both of the first optical frequency comb C1 generated by the first optical microresonator 21 and the second optical frequency comb C2 generated by the second optical microresonator 22 may be output through the output coupler 31.

Referring to FIG. 11, an optical dual-comb source apparatus 20c may include two lasers 19 and 20, two optical microresonators 21 and 22, and two input/output couplers 27 and 28. For example, the first input/output coupler 27 may be arranged to contact an outer periphery of the first optical microresonator 21, and the second input/output coupler 28 may be arranged to contact an outer periphery of the second optical microresonator 22. The first laser light 24 emitted by the first laser 19 may be supplied to the first optical microresonator 21 through the first input/output coupler 27, and the second laser light 25 emitted by the second laser 20 may be supplied to the second optical microresonator 22 through the second input/output coupler 28. Thereafter, the first optical frequency comb C1 generated by the first optical microresonator 21 may be output through the first input/output coupler 27, and the second optical frequency comb C2 generated by the second optical microresonator 22 may be output through the second input/output coupler 28.

Referring to FIG. 12, an optical dual-comb source apparatus 20d may include two lasers 19 and 20, a beam coupler 11, an input/output coupler 27, and an optical microresonator 21. The optical microresonator 21 may have a plurality of resonance modes with different resonance frequencies. For example, the optical microresonator 21 may have different effective resonator radii depending on depths from a surface thereof. The first laser 19 may emit first laser light 24 having a spectrum component corresponding to a resonance frequency of a resonance mode related to a first optical frequency comb C1, from among a plurality of different resonance modes of the optical microresonator 21. Also, the second laser 20 may emit second laser light 25 having a spectrum component corresponding to a resonance frequency of a resonance mode related to a second optical frequency comb C2, from among the plurality of different resonance modes of the optical microresonator 21.

The beam coupler 11 may couple the first laser light 24 emitted by the first laser 19 and the second laser light 25 emitted by the second laser 20 to propagate a coupling result thereof through an optical path. Then, the first laser light 24 and the second laser light 25 may be provided to the optical microresonator 21 through the input/output coupler 27. Also, the first optical frequency comb C1 and the second optical frequency comb C2 emitted by the optical microresonator 21 may be output again through the input/output coupler 27.

Referring to FIG. 13, an optical dual-comb source apparatus 20e may include two lasers 19 and 20, an input coupler 29, an input/output coupler 27, and an optical microresonator 21. The optical microresonator 21 may have a plurality of resonance modes with different resonance frequencies. The first laser 19 may emit first laser light 24 having a spectrum component corresponding to a resonance frequency of a resonance mode related to the first optical frequency comb C1. The second laser 20 may emit second laser light 25 having a spectrum component corresponding to a resonance frequency of a resonance mode related to the second optical frequency comb C2.

The input coupler 29 may be configured to supply the second laser light 25 emitted by the second laser 20 to the optical microresonator 21. The input/output coupler 27 may be configured to supply the first laser light 24 emitted by the first laser 19 to the optical microresonator 21 and output the first and second optical frequency combs C1 and C2 generated by the optical microresonator 21. Thus, the first laser light 24 and the second laser light 25 may be supplied to the optical microresonator 21 through different optical paths, while the first optical frequency comb C1 and the second optical frequency comb C2 output from the optical microresonator 21 may propagate through an optical path.

Referring to FIG. 14, an optical dual-comb source apparatus 20f may include two lasers 19 and 20, two input/output couplers 27 and 28, and an optical microresonator 21 having a plurality of resonance modes with different resonance frequencies. In this structure, the first laser light 24 emitted by the first laser 19 may be supplied to the optical microresonator 21 through the first input/output coupler 27, and the first optical frequency comb C1 generated by the optical microresonator 21 may be output through the first input/output coupler 27. Also, the second laser light 25 emitted by the second laser 20 may be supplied to the optical microresonator 21 through the second input/output coupler 28, and the second optical frequency comb C2 generated by the optical microresonator 21 may be output through the second input/output coupler 28.

Since the above optical dual-comb source apparatuses 10a to 10e and 20a to 20f may generate optical frequency combs by using only optical resonators, they may not require additional external high frequency generators. Thus, the optical dual-comb source apparatuses 10a to 10e and 20a to 20f may be manufactured simply and may be used in any of various measurement apparatuses. For example, FIGS. 15 to 18 are schematic block diagrams illustrating various optical measurement apparatuses using dual optical frequency combs generated by the optical dual-comb source apparatuses 10a to 10e and 20a to 20f.

Figure 15:
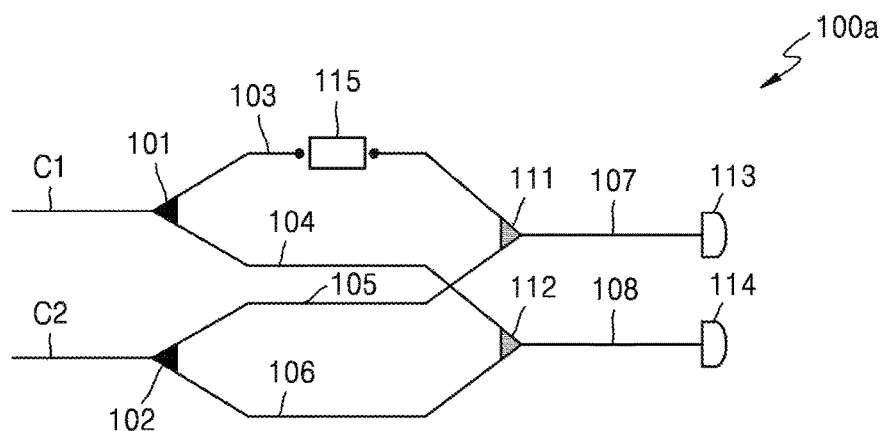
FIG. 15 is a schematic block diagram illustrating an optical measurement apparatus using a dual optical frequency comb, according to an exemplary embodiment.

First, referring to FIG. 15, an optical measurement apparatus 100a may include first and second beam splitters 101 and 102, first and second beam couplers 111 and 112, and first and second photodetectors 113 and 114. The first beam splitter 101 may split a first optical frequency comb C1 into a probe frequency comb 103 and a reference frequency comb 104. The second beam splitter 102 may split a second optical frequency comb C2 into two optical frequency combs 105 and 106. The first and second optical frequency combs C1 and C2 may be provided from one of the above optical dual-comb source apparatuses 10a to 10e and 20a to 20f. The probe frequency comb 103 may be irradiated onto a measurement target 115 to pass through the measurement target 115 or to be reflected or scattered by the measurement target 115. The first beam coupler 111 may generate a third optical frequency comb 107 by coupling the probe frequency comb 103, which has been transmitted through or been reflected or scattered by the measurement target 115, to one of the split second optical frequency combs 105. The second beam coupler 112 may generate a fourth optical frequency comb 108 by coupling the reference frequency comb 104 to another of the split second optical frequency combs 106. The generated third and fourth optical frequency combs 107 and 108 may each have a beat pattern. The first photodetector 113 and the second photodetector 114 may respectively measure the third optical frequency comb 107 and the fourth optical frequency comb 108. As for the probe frequency comb 103, that has been transmitted through or reflected or scattered by the measurement target 115, a spectral envelope thereof may be modulated or a delay may occur therein. Thus, a calculator or processor (not illustrated) may extract information about the measurement target 115 by comparing a difference between a beat pattern of the fourth optical frequency comb 108 and an interference pattern of the third optical frequency comb 107 in a frequency domain.

Figure 16:
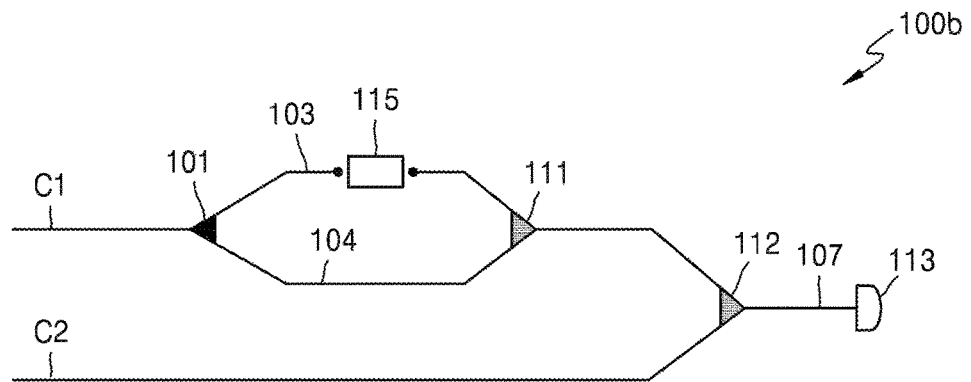
FIGS. 16, 17, and 18 are schematic block diagrams illustrating optical measurement apparatuses using a dual optical frequency comb, according to other exemplary embodiments.

Also, referring to FIG. 16, an optical measurement apparatus 100b may include a beam splitter 101, a first beam coupler 111, a second beam coupler 112, and a photodetector 113. The beam splitter 101 may split a first optical frequency comb C1 into a probe frequency comb 103 and a reference frequency comb 104. The probe frequency comb 103 may be irradiated onto a measurement target 115. The first beam coupler 111 may couple the probe frequency comb 103, which has been transmitted through or reflected or scattered by the measurement target 115, to the reference frequency comb 104. Then, the probe frequency comb 103 and the reference frequency comb 104 may interfere with each other to generate an interference pattern. Thereafter, the second beam coupler 112 may couple the probe frequency comb 103 and the reference frequency comb 104 to a second optical frequency comb C2 to generate a third optical frequency comb 107. The photodetector 113 may measure the third optical frequency comb 107. Then, a calculator or processor (not illustrated) may extract information about the measurement target 115 by analyzing a frequency pattern of the third optical frequency comb.

Figure 17:
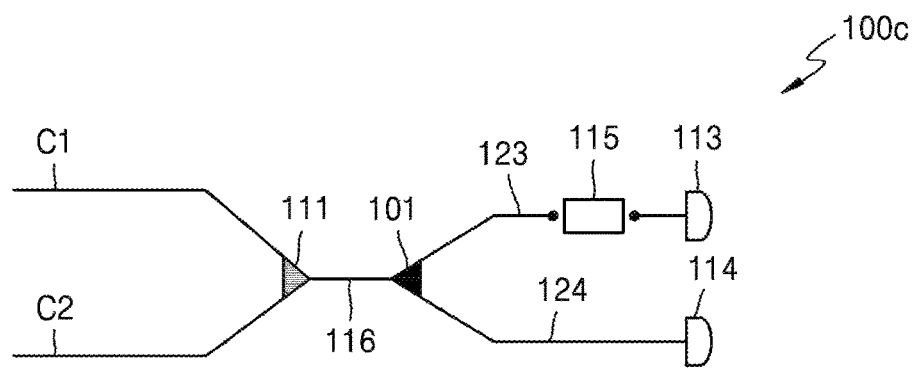

Referring to FIG. 17, an optical measurement apparatus 100c may include a beam coupler 111, a beam splitter 101, a first photodetector 113, and a second photodetector 114. The beam coupler 111 may couple a first optical frequency comb C1 and a second optical frequency comb C2 to generate a frequency comb 116. The beam splitter 101 may split the frequency comb 116 into a probe frequency comb 123 and a reference frequency comb 124. Each of the probe frequency comb 123 and the reference frequency comb 124 may have both a component of the first optical frequency comb C1 and a component of the second optical frequency comb C2. The probe frequency comb 123 may be irradiated onto a measurement target 115. The first photodetector 113 may measure the probe frequency comb 123 that has been transmitted through or reflected or scattered by the measurement target 115. The second photodetector 114 may measure the reference frequency comb 124 split by the beam splitter 101. Then, a calculator or processor (not illustrated) may extract information about the measurement target 115 by comparing a difference between the probe reference comb 123 and the reference frequency comb 124 in a frequency domain.

Figure 18:
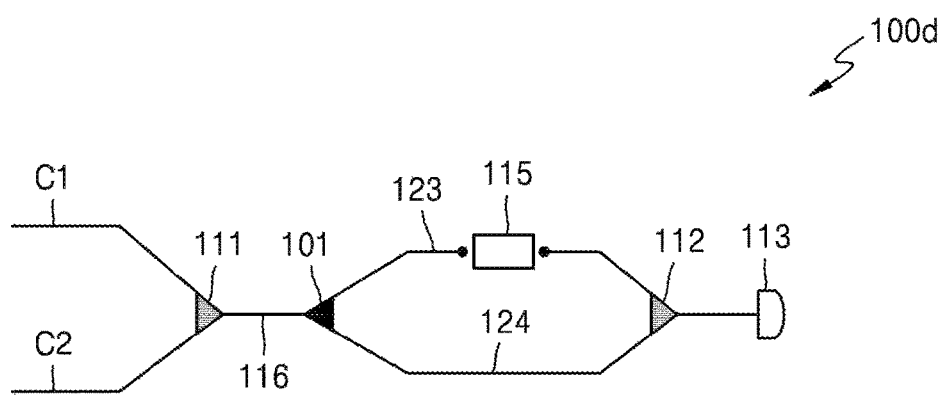

Referring to FIG. 18, an optical measurement apparatus 100d may include a first beam coupler 111, a beam splitter 101, a second beam coupler 112, and a photodetector 113. The first beam coupler 111 may couple a first optical frequency comb C1 and a second optical frequency comb C2 to generate a frequency comb 116. The beam splitter 101 may split the frequency comb 116 into a probe frequency comb 123 and a reference frequency comb 124. The probe frequency comb 123 may be irradiated onto a measurement target 115. The second beam coupler 112 may couple the probe frequency comb 123, which has been transmitted through or reflected or scattered by the measurement target 115, to the reference frequency comb 124. The photodetector 113 may measure the coupled probe frequency comb 123 and reference frequency comb 124. Then, a calculator or processor (not illustrated) may extract information about the measurement target 115 by analyzing a frequency pattern of the coupled probe reference comb 123 and reference frequency comb 124.

The optical dual-comb source apparatuses including the optical microresonators according to the exemplary embodiments have been described above with reference to the drawings. However, these are merely exemplary, and those of ordinary skill in the art will understand that various modifications and other equivalent embodiments may be derived therefrom. Therefore, the above exemplary embodiments should be considered in descriptive sense only and not for purposes of limitation. Thus, the scope of the inventive concept may be defined not by the above detailed descriptions but by the appended claims, and all differences within the scope will be construed as being included in the inventive concept.

It should be understood that embodiments described herein should be considered in a descriptive sense only and not for purposes of limitation. Descriptions of features or aspects within each exemplary embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An optical dual-comb source apparatus comprising:
laser light source configured to output first laser light and second laser light; and
an optical microresonator comprising a nonlinear material with a refractive index which is variable based on a light intensity, wherein the optical microresonator has a plurality of different resonance modes,
wherein
the optical microresonator is configured to interact with the first laser light and the second laser light and thereby generate a first optical frequency comb and a second optical frequency comb, the second optical frequency comb having a mode interval different from a mode interval of the first optical frequency comb, and
the first laser light has a spectrum component corresponding to a resonance frequency of a resonance mode related to the first optical frequency comb and the second laser light has a spectrum component corresponding to a resonance frequency of a resonance mode related to the second optical frequency comb.

2. The optical dual-comb source apparatus of claim 1, wherein the optical microresonator is disk-shaped and has a plurality of different resonance modes according to a depth from a surface of the optical microresonator.

3. The optical dual-comb source apparatus of claim 1, wherein the laser light source comprises a continuous wave laser having a multimode in which at least two transverse modes or at least two longitudinal modes of light are simultaneously emitted.

4. The optical dual-comb source apparatus of claim 3, further comprising an input/output coupler configured to input the first laser light and the second laser light emitted by the continuous wave laser into the optical microresonator and configured to output the first optical frequency comb and the second optical frequency comb generated by the optical microresonator.

5. The optical dual-comb source apparatus of claim 1, wherein the laser light source comprises:
a continuous wave laser configured to emit the first laser light; and
an electrooptical modulator configured to modulate the first laser light to generate an optical sideband corresponding to a resonance frequency of a resonance mode related to the second optical frequency comb.

6. The optical dual-comb source apparatus of claim 1, wherein the laser light source comprises:
a first continuous wave laser configured to emit the first laser light; and
a second continuous wave laser configured to emit the second laser light.

7. The optical dual-comb source apparatus of claim 6, further comprising:
a beam coupler configured to couple the first laser light and the second laser light to propagate a coupling result thereof through an optical path; and
an input/output coupler configured to input the first laser light and the second laser light into the optical microresonator and to output the first optical frequency comb and the second optical frequency comb generated by the optical microresonator.

8. The optical dual-comb source apparatus of claim 6, further comprising:
an input/output coupler configured to input the first laser light to the optical microresonator and to output the first optical frequency comb and the second optical frequency comb generated by the optical microresonator; and
an input coupler configured to input the second laser light into the optical microresonator.

9. The optical dual-comb source apparatus of claim 6, further comprising:
a first input/output coupler configured to input the first laser light into the optical microresonator and to output the first optical frequency comb generated by the optical microresonator; and
a second input/output coupler configured to input the second laser light into the optical microresonator and to output the second optical frequency comb generated by the optical microresonator.

10. An optical dual-comb source apparatus comprising:
laser light source configured to output first laser light and second laser light; and
a first optical microresonator and a second optical microresonator, each comprising a nonlinear material with a refractive index which is variable based on a light intensity,
wherein
the first optical microresonator and the second optical microresonator are each configured to interact with the first laser light and the second laser light and thereby generate a first optical frequency comb and a second optical frequency comb having different mode intervals, and
the first laser light has a spectrum component corresponding to a resonance frequency of a resonance mode related to the first optical frequency comb and the second laser light has a spectrum component corresponding to a resonance frequency of a resonance mode related to the second optical frequency comb.

11. The optical dual-comb source apparatus of claim 10, wherein the laser light source comprises a continuous wave laser having a multimode in which at least two transverse modes or at least two longitudinal modes of light are simultaneously emitted.

12. The optical dual-comb source apparatus of claim 11, further comprising an input/output coupler configured to input the first laser light and the second laser light emitted by the continuous wave laser into each of the first optical microresonator and the second optical microresonator and to output the first optical frequency comb and the second optical frequency comb generated by the first and second optical microresonators.

13. The optical dual-comb source apparatus of claim 10, wherein the laser light source comprises:
a continuous wave laser configured to emit the first laser light; and
an electrooptical modulator configured to modulate the first laser light to generate an optical sideband corresponding to a resonance frequency of a resonance mode related to the second optical frequency comb.

14. The optical dual-comb source apparatus of claim 10, wherein the first optical microresonator and the second optical microresonator each comprise a disk-shaped resonator having a plurality of different resonance modes according to a depth from a surface of the respective optical microresonator.

15. The optical dual-comb source apparatus of claim 10, wherein
the first optical microresonator has a resonance mode related to the first optical frequency comb,
the second optical microresonator has a resonance mode related to the second optical frequency comb,
the first optical microresonator and the second optical microresonator are each disk-shaped;
the first optical microresonator has a diameter that is different from a diameter of the second optical microresonator.

16. The optical dual-comb source apparatus of claim 15, wherein
the laser light source comprises a continuous wave laser having a multimode in which at least two transverse modes or at least two longitudinal modes of laser light are simultaneously emitted, and
the optical dual-comb source apparatus further comprises:
an input coupler configured to input the first laser light and the second laser light emitted by the continuous wave laser into each of the first and second optical microresonators;
a first output coupler configured to output the first optical frequency comb generated by the first optical microresonator; and
a second output coupler configured to output the second optical frequency comb generated by the second optical microresonator.

17. The optical dual-comb source apparatus of claim 15, wherein
the laser light source comprises a continuous wave laser having a multimode in which at least two transverse modes or at least two longitudinal modes of laser light are simultaneously emitted, and
the optical dual-comb source apparatus further comprises:
a first input/output coupler configured to input the laser light emitted by the continuous wave laser into the first optical microresonator and to output the first optical frequency comb generated by the first optical microresonator; and
a second input/output coupler configured to input the laser light emitted by the continuous wave laser into the second optical microresonator and to output the second optical frequency comb generated by the second optical microresonator.

18. The optical dual-comb source apparatus of claim 15, wherein
the laser light source comprises a continuous wave laser having a multimode in which at least two transverse modes or at least two longitudinal modes of laser light are simultaneously emitted, and
the optical dual-comb source apparatus further comprises:
a first input coupler configured to input the laser light emitted by the continuous wave laser into the first optical microresonator;
a second input coupler configured to input the laser light emitted by the continuous wave laser into the second optical microresonator;
a first output coupler configured to output the first optical frequency comb generated by the first optical microresonator; and
a second output coupler configured to output the second optical frequency comb generated by the second optical microresonator.

19. The optical dual-comb source apparatus of claim 15, wherein the laser light source comprises:
   a first continuous wave laser configured to emit the first laser light; and
   a second continuous wave laser configured to emit the second laser light.

20. The optical dual-comb source apparatus of claim 19, further comprising:
   a first input coupler configured to input the first laser light to the first optical microresonator;
   a second input coupler configured to input the second laser light to the second optical microresonator;
   a first output coupler configured to output the first optical frequency comb generated by the first optical microresonator; and
   a second output coupler configured to output the second optical frequency comb generated by the second optical microresonator.

21. The optical dual-comb source apparatus of claim 19, further comprising:
   a first input coupler configured to input the first laser light emitted by the first continuous wave laser into the first optical microresonator;
   a second input coupler configured to input the second laser light emitted by the second continuous wave laser into the second optical microresonator; and
   an output coupler configured to output the first optical frequency comb and the second optical frequency comb generated respectively by the first optical microresonator and the second optical microresonator.

22. The optical dual-comb source apparatus of claim 19, further comprising:
   a first input/output coupler configured to input the first laser light into the first optical microresonator and to output the first optical frequency comb generated by the first optical microresonator; and
   a second input/output coupler configured to input the second laser light into the second optical microresonator and output the second optical frequency comb generated by the second optical microresonator.

23. An optical measurement apparatus comprising:
   an optical dual-comb source apparatus configured to generate a first optical frequency comb and a second optical frequency comb, wherein a mode interval of the first optical frequency comb is different from a mode interval of the second optical frequency comb;
   a first beam splitter configured to split the first optical frequency comb into a probe frequency comb and a reference frequency comb;
   a second beam splitter configured to split the second optical frequency comb into two second optical frequency combs;
   a first beam coupler configured to generate a third optical frequency comb by coupling the probe frequency comb, which is transmitted through or reflected or scattered by a measurement target, to a first one of the second optical frequency combs;
   a second beam coupler configured to generate a fourth optical frequency comb by coupling the reference frequency comb to a second one of the split second optical frequency combs;
   a first photodetector configured to measure the third optical frequency comb; and
   a second photodetector configured to measure the fourth optical frequency comb,
   wherein the optical dual-comb source apparatus comprises:
   laser light source configured to provide first laser light and second laser light; and
   an optical microresonator comprising a nonlinear material with a refractive index which is variable based on a light intensity, wherein the optical microresonator has a plurality of different resonance modes,
   wherein
   the optical microresonator is configured to interact with the first laser light and the second laser light and thereby generate a first optical frequency comb and a second optical frequency comb, wherein a mode interval of the first optical frequency comb is different that a mode interval of the second optical frequency comb, and
   the first laser light has a spectrum component corresponding to a resonance frequency of a resonance mode related to the first optical frequency comb and the second laser light has a spectrum component corresponding to a resonance frequency of a resonance mode related to the second optical frequency comb.

24. An optical measurement apparatus comprising:
   an optical dual-comb source apparatus configured to generate a first optical frequency comb and a second optical frequency comb, wherein the first optical frequency comb has a mode interval different from a mode interval of the second optical frequency comb;
   a first beam splitter configured to split the first optical frequency comb into a probe frequency comb and a reference frequency comb;
   a first beam coupler configured to couple the probe frequency comb, which is transmitted through or reflected or scattered by a measurement target, to the reference frequency comb;
   a second beam coupler configured to generate a third optical frequency comb by coupling the probe frequency comb and the reference frequency comb coupled by the first beam coupler to the second optical frequency comb; and
   a photodetector configured to measure the third optical frequency comb,
   wherein the optical dual-comb source apparatus comprises:
   laser light source configured to output first laser light and second laser light; and
   an optical microresonator comprising a nonlinear material with a refractive index which is variable based on a light intensity, wherein the optical microresonator has a plurality of different resonance modes,
   wherein
   the optical microresonator is configured to generate the first optical frequency comb and the second optical frequency comb by interacting with the first laser light and the second laser light, and
   the first laser light has a spectrum component corresponding to a resonance frequency of a resonance mode related to the first optical frequency comb and the second laser light has a spectrum component corresponding to a resonance frequency of a resonance mode related to the second optical frequency comb.

25. An optical measurement apparatus comprising:
   an optical dual-comb source apparatus configured to generate a first optical frequency comb and a second optical frequency comb, wherein a mode interval of the first optical frequency comb is different than a mode interval of the second optical frequency comb;

a beam coupler configured to couple the first optical frequency comb and the second optical frequency comb to generate a frequency comb;

a beam splitter configured to split the generated frequency comb into a probe frequency comb and a reference frequency comb;

a first photodetector configured to measure the probe frequency comb that is transmitted through or reflected or scattered by a measurement target; and a second photodetector configured to measure the reference frequency comb, wherein the optical dual-comb source apparatus comprises:

laser light source configured to provide a first laser light and a second laser light; and an optical microresonator comprising a nonlinear material with a refractive index which varies based on a light intensity, wherein the optical microresonator has a plurality of different resonance modes, wherein the optical microresonator is configured to generate the first optical frequency comb and the second optical frequency comb by interacting with the first laser light and the second laser light, and the first laser light has a spectrum component corresponding to a resonance frequency of a resonance mode related to the first optical frequency comb and the second laser light has a spectrum component corresponding to a resonance frequency of a resonance mode related to the second optical frequency comb.

* * * * *